United States Patent
Williams et al.

(10) Patent No.: US 7,511,155 B2
(45) Date of Patent: Mar. 31, 2009

(54) REAGENTS AND A METHOD FOR SATURATION LABELLING OF PROTEINS

(75) Inventors: Karen Williams, Amersham (GB); Timothy Stone, Amersham (GB); Adrian Christopher Simmonds, Amersham (GB); Alison Claire Sweet, Giles (GB); Susan Janet Fowler, Amersham (GB)

(73) Assignee: GE Healthcare UK Limited, Amersham (GB)

( * ) Notice: Subject to any disclaimer, the term of this patent is extended or adjusted under 35 U.S.C. 154(b) by 581 days.

(21) Appl. No.: 10/519,433

(22) PCT Filed: Jul. 8, 2002

(86) PCT No.: PCT/GB02/03142

§ 371 (c)(1), (2), (4) Date: Jun. 23, 2005

(87) PCT Pub. No.: WO2004/005933

PCT Pub. Date: Jan. 15, 2004

(65) Prior Publication Data

US 2005/0233462 A1    Oct. 20, 2005

(51) Int. Cl.
C09B 23/02 (2006.01)
C09B 67/22 (2006.01)
G01N 33/68 (2006.01)

(52) U.S. Cl. ...................... 548/427; 548/455
(58) Field of Classification Search ............. None
See application file for complete search history.

(56) References Cited

U.S. PATENT DOCUMENTS

| | | | |
|---|---|---|---|
| 5,268,486 A | 12/1993 | Waggoner et al. | |
| 6,127,134 A | 10/2000 | Minden et al. | |
| 6,224,644 B1 * | 5/2001 | Randall et al. | 548/152 |
| 6,825,195 B2 * | 11/2004 | Kimura | 514/237.2 |
| 6,977,305 B2 * | 12/2005 | Leung et al. | 548/450 |
| 2002/0077487 A1 * | 6/2002 | Leung et al. | 548/414 |
| 2007/0042398 A1 * | 2/2007 | Peng et al. | 435/6 |

FOREIGN PATENT DOCUMENTS

EP    1038938    *  9/2000

OTHER PUBLICATIONS

Suzuki et al., FEBS Letters, 512(1-3), 235-239, 2002.*
Ernst, L., et al., "Cyanine Dye Labeling Reagents for Sulfhydryl Groups", *Cytometry*, vol. 10, No. 1, 1989, p. 3-10.

* cited by examiner

*Primary Examiner*—Fiona T Powers
(74) *Attorney, Agent, or Firm*—Yonggang Ji

(57) ABSTRACT

A matched set of fluorescent dyes is provided, wherein each dye of the set is capable of covalent attachment to a protein and wherein each of the dyes has a molecular structure and a charge that is matched one with the other, such that relative electrophoretic mobility of a protein labeled with one dye of the set is the same as the electrophoretic mobility of the protein labeled with a different dye of the set. The matched set comprises at least two different fluorescent dyes of formula:

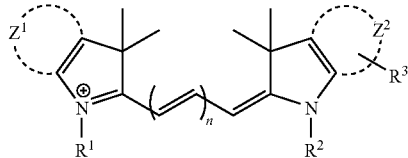

wherein n is 1, 2, or 3; $Z^1$ and $Z^2$ independently represent the carbon atoms necessary to complete a phenyl or naphthyl ring system; one of groups $R^1$ and $R^2$ is a target bonding group; remaining group $R^1$ or $R^2$ is selected from —$(CH_2)_4$—W or —$(CH_2)_r$—H; group $R^3$ is hydrogen, except when either $R^1$ or $R^2$ is —$(CH_2)_r$—H, in which case $R^3$ is W; and W is selected from sulphonic acid and sulphonate. The invention also provides a method for saturation labeling of a protein with a fluorescent dye so as to label all available target amino acid, suitably cysteine, residues in the protein, thereby giving a single population of labeled protein molecules.

7 Claims, 2 Drawing Sheets

Figure 2
Overlay Images of Proteins Labelled with Dye Sets 1, 12 and 9 and Separated by 2D Electrophoresis with Outlines of Labelled Protein Spots to Demonstrate Positional Matching
Overlay of Preferred Dye Set 1
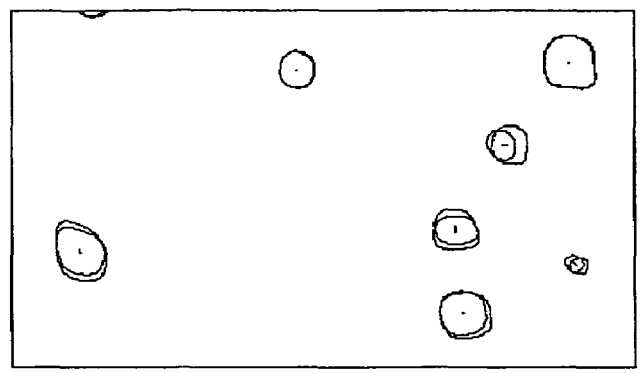
Overlay of Dye Set 12
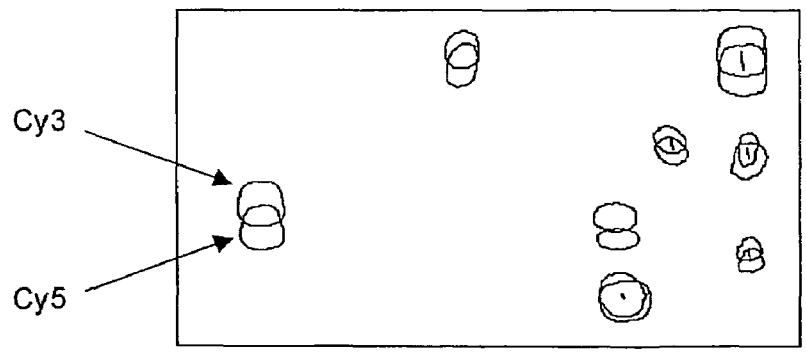
Overlay of Dye Set 9
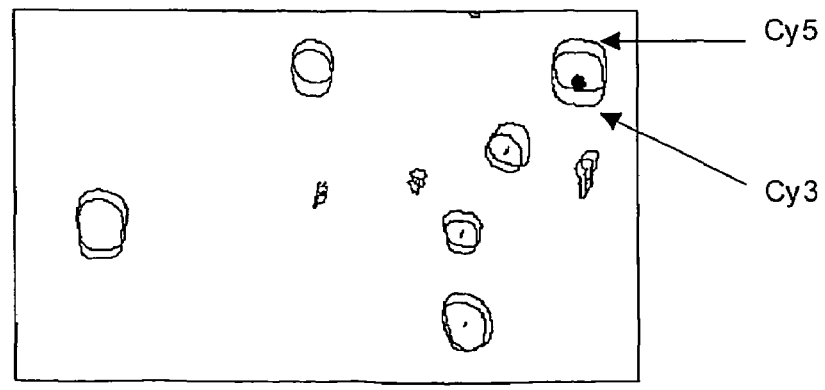

REAGENTS AND A METHOD FOR SATURATION LABELLING OF PROTEINS

CROSS REFERENCE TO RELATED APPLICATIONS

This application is a filing under 35 U.S.C. § 371 and claims priority to international patent application number PCT/GB2002/003142 filed Jul. 8, 2002, published on Jan. 15, 2004 as WO 2004/005933; the disclosure of which is incorporated herein by reference in its entirety.

The present invention relates to fluorescent dyes and to a method for labelling complex protein samples to enable differential protein analysis.

2D Difference Gel Electrophoresis (DIGE) uses matched, spectrally-resolved fluorescent dyes to label protein samples prior to 2-dimensional (2D) electrophoretic separation (Minden, J. et al, Electrophoresis, (1997), 18, 2071). This fluorescent multiplexing approach overcomes many of the disadvantages of traditional 2D electrophoresis. Fluorescent pre-labelling of protein samples allows multiple samples to be run on the same gel, enabling quantitative differences between the samples to be easily identified by overlaying the fluorescent images. To allow fluorescent multiplexing, the protein samples must be labelled equally with the dyes and the migration of the labelled proteins in the gel must be positionally matched, to allow quantitative differences to be detected.

WO 96/33406 (Minden, J. et al) discloses a method to detect differences between different cell samples using matched, spectrally resolved dyes to label protein in the samples prior to 2D electrophoresis. Described are dyes that are matched for molecular mass and charge to give equivalent migration. The approach employs cyanine dyes having an N-hydroxysuccinimidyl (NHS) ester reactive group to label amines. The NHS ester group is targeted at the ε-amino of lysine residues in proteins and results in covalent labelling. Three different dyes (Cy2™, Cy3 and Cy5) are derivatised to enable multiplexing. These dye molecules have a molecular weight of approximately 500 Daltons and are matched in mass to give equivalent migration of the labelled protein. The dyes rely on the intrinsic charge of the cyanine fluor to compensate for the loss of a lysine positive charge on conjugation of the dye to lysine. WO 96/33406 describes the use of these dyes in a minimal labelling strategy to label between 1 and 2% of available attachment sites. To achieve equivalent migration, the dye pairs were matched for mass by compensating for the difference in the linker length between the indole rings of the cyanine by modulation of the size of the aliphatic chain attached to an indole nitrogen by 2 carbon units. Two or more spectrally resolved dyes that meet these criteria represent a matched minimal labelling dye set. Equivalent migration of the matched lysine minimal labelling dye set was demonstrated using propyl Cy3 and methyl Cy5 to label proteins followed by their 2D separation and overlaying the resulting images to show positional matching of the two labelled samples.

Lysine residues are highly abundant in proteins, ensuring that this labelling strategy will represent all the proteins present in a complex is sample. However, the typical lysine content of a protein is 7% and, if every lysine in a protein were labelled, it would result in a large mass shift due to the dye. Thus, the strategy employed is to "minimally" label the protein to ensure that only ~1 in 5 protein molecules are labelled, thereby giving a statistical probability that each labelled molecule has only one dye attached. This creates a spot pattern on 2D that is very similar to silver stained images, but gives greater sensitivity and dynamic range and the ability to multiplex.

A typical 2D gel analysis involves "picking" protein spots of interest from the gel for identification by MALDI-MS. The minimal labelling approach results in 2 spots per protein (ie. labelled and unlabelled), with the majority of protein in the unlabelled spot. The unlabelled spot must be located to recover sufficient protein to enable identification by MALDI-MS. This requires an additional staining step prior to spot picking. In order to facilitate protein spot picking directly from fluorescent gels, a labelling strategy is required that gives a single spot per protein.

The labelling strategy employed in the present invention aims to saturate the protein with dye in order to label as many target residues as possible and to produce a single labelled spot per protein isoform. Thus, a cyanine dye molecule is coupled to all available target amino acid residues on a protein, thereby giving a single population of labelled protein molecules with a similar number of dye molecules attached. According to the present invention, saturation labelling is achieved using dye sets targeted at cysteine residues, which contain a thiol group. Cysteine residues are present in 95% of proteins, but there are fewer cysteine residues in each protein than lysine. This means that all protein molecules can be labelled, but each protein molecule will have fewer labelled residues than if lysine residues were labelled to saturation. This results in increased sensitivity of detection as the proportion of labelled protein is higher than with minimal labelling, but ensures that the proteins remain soluble.

The increase in mass due to the addition of dye (the mass shift) with saturation labelling of cysteine residues will be larger than that employing a minimal labelling strategy of lysine residues. However, the increase in mass is less than would be observed if a saturation labelling approach was employed on lysine residues. The extent of the mass shift due to the dye addition will vary for each protein depending on the individual protein cysteine content (typically ~2%) and the availability of the cysteine residues to the dye under the conditions of labelling. This results in a 2D spot pattern that is very different from published silver stained 2D protein maps.

The present invention therefore provides fluorescent reagents and a method for reproducibly labelling, all of the available cysteine residues that are accessible in a mixture of cysteine-containing proteins. The cyanine dye derivatives according to the present invention provide valuable sets of fluorescent labels, each having a common core structure and which are particularly useful for multiplex analysis.

Accordingly, in a first aspect, the present invention provides a matched set of fluorescent dyes comprising at least two different fluorescent dyes having the formula (I):

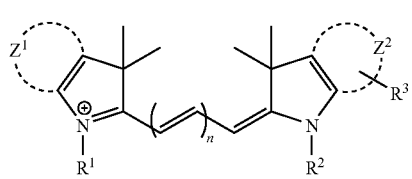

wherein n is different for each said dye and is 1, 2, or 3;
$Z^1$ and $Z^2$ independently represent the carbon atoms necessary to complete a phenyl or naphthyl ring system;

one of groups $R^1$ and $R^2$ is the group:

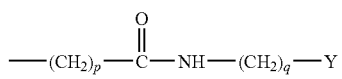

where Y is a target bonding group;
remaining group $R^1$ or $R^2$ is selected from —(CH$_2$)$_4$—W or —(CH$_2$)$_r$—H;
group $R^3$ is hydrogen, except when either $R^1$ or $R^2$ is —(CH$_2$)$_r$—H, in which case $R^3$ is W;
W is selected from sulphonic acid and sulphonate;
p is an integer from 3 to 6;
q is selected to be 2 or 3; and
r is an integer from 1 to 5;
and their salts;
characterised in that when n of two of said dyes differs by +1, one of p, q and r of said two dyes differs by −1.

According to the present invention a matched set of fluorescent dyes is provided, wherein each dye of the set is capable of covalent attachment to a protein and wherein each of the dyes has a molecular structure and a charge that is matched one with the other, such that relative electrophoretic mobility of a protein labelled with one dye of the set is the same or substantially the same as the electrophoretic mobility of the protein labelled with a different dye of the same set. In one embodiment according to the first aspect, the matched set of dyes comprises at least two different fluorescent dyes, wherein each dye in said set is a compound having the formula (I) and wherein $Z^1$, $Z^2$, $R^1$, $R^2$, $R^3$, Y, W, n, p, q and r are hereinbefore defined. Suitably, the different dyes in the matched set of fluorescent dyes are spectrally resolvable to enable different samples labelled with such dyes to be distinguished one from the other. Suitably, at least two dyes of the matched set of dyes have a structure according to formula (I) and may be selected from the trimethine cyanine dye class (in which n=1), the pentamethine cyanine dye class (in which n=2) and the heptamethine cyanine dyes (in which n=3).

Suitably, the matched set of fluorescent dyes according to the invention comprises at least two different fluorescent dyes having the formula (II):

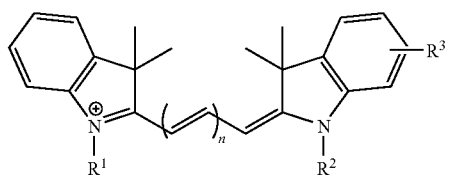

(II)

wherein n is different for each said dye and is 1, 2, or 3;
one of groups $R^1$ and $R^2$ is the group:

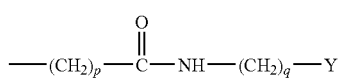

where Y is a target bonding group;
remaining group $R^1$ or $R^2$ is selected from —(CH$_2$)$_4$—W or —(CH$_2$)$_r$—H;
group $R^3$ is hydrogen, except when either $R^1$ or $R^2$ is —(CH$_2$)$_r$—H, in which case $R^3$ is W;
W is selected from sulphonic acid and sulphonate;
p is an integer from 3 to 6;
q is selected to be 2 or 3; and
r is an integer from 1 to 5; and their salts;
characterised in that when n of two of said dyes differs by +1, one of p, q and r of said two dyes differs by −1.

Preferably, the matched set of fluorescent dyes comprises at least two different dyes according to formula (I) or (II) in which:
n is selected to be 1 or 2;
p is selected to be 4 or 5;
q is selected to be 2 or 3; and
r is selected to be 1, 2 or 3.

Preferably, the target bonding group Y in each dye of the matched set of fluorescent dyes is the same and is selected from a maleimido group and an iodoacetamido group. A particularly preferred target bonding group for each dye is a maleimido group.

Particularly preferred are dye sets according to formula (I) or (II) that are selected from the trimethine cyanine class of dyes and the pentamethine cyanine class of dyes. Such dyes are described as Cy3™ and Cy5 dyes. Absorbance and emission data for the cyanine dyes are shown below in Table 1.

TABLE 1

| Dye | Fluorescence Colour | Abs (nm) | Em (nm) |
| --- | --- | --- | --- |
| Cy3 | Orange | 550 | 570 |
| Cy5 | Far red | 649 | 670 |
| Cy7 | Near IR | 747 | 774 |

Suitably, salts of the fluorescent dyes according to formula (I) or (II) may be selected from K$^+$, Na$^+$, NH$_4^+$, R$_3$NH$^+$ and R$_4$N$^+$ where R is C$_1$ to C$_4$ alkyl.

In an alternative embodiment, the matched set of dyes may optionally include one or more additional dyes, provided that each such additional dye possesses charge and mass characteristics, such that the electrophoretic mobility of a protein labelled with the dye is the same or substantially the same as the electrophoretic mobility of a protein labelled with a dye according to formula (I) or (II). Other such additional dyes may include benzoxazole-containing dyes. An example of an additional dye is Cy2.

Exemplary sets containing pairs of fluorescent dyes according to formula (I) or (II) that are matched in electrophoretic mobility when coupled to proteins are as follows:

Set 1
1-(6-{[2-(2,5-dioxo-2,5-dihydro-1H-pyrrol-1-yl)ethyl]amino}-6-oxohexyl)-2-[(1E,3E)-3-(1-ethyl-3,3-dimethyl-5-sulpho-1,3-dihydro-2H-indol-2-ylidene)prop-1-enyl]-3,3-dimethyl-3H-indolium (Compound I); and
1-(6-{[2-(2,5-dioxo-2,5-dihydro-1H-pyrrol-1-yl)ethyl]amino}-6-oxohexyl)-3,3-dimethyl-2-[(1E,3E,5E)-5-(1,3,3-trimethyl-5-sulpho-1,3-dihydro-2H-indol-2-ylidene)penta-1,3-dienyl]-3H-indolium (Compound II);

Set 2
1-(6-{[2-(2,5-dioxo-2,5-dihydro-1H-pyrrol-1-yl)ethyl]amino}-6-oxohexyl)-2-[(1E,3E)-3-(1-propyl-3,3-dimethyl-5-sulpho-1,3-dihydro-2H-indol-2-ylidene)prop-1-enyl]-3,3-dimethyl-3H-indolium (Compound III); and
1-(6-{[2-(2,5-dioxo-2,5-dihydro-1H-pyrrol-1-yl)ethyl]amino}-6-oxohexyl)-3,3-dimethyl-2-[(1E,3E,5E)-5-(1- ethyl-3,3-trimethyl-5-sulpho-1,3-dihydro-2H-indol-2-ylidene)penta-1,3-dienyl]-3H-indolium (Compound IV);

Set 3
1-(6-{[2-(2,5-dioxo-2,5-dihydro-1H-pyrrol-1-yl)ethyl]amino}-6-oxohexyl)-2-[(1E,3E)-3-( 1-ethyl-3,3-dimethyl-5-sulpho-1,3-dihydro-2H-indol-2-ylidene)prop-1-enyl]-3,3-dimethyl-3H-indolium (Compound I); and
1-(5-{[2-(2,5-dioxo-2,5-dihydro-1H-pyrrol-1-yl)ethyl]amino}-6-oxopentyl)-3,3-dimethyl-2-[(1E,3E,5E)-5-( 1-ethyl-3,3-trimethyl-5-sulpho-1,3-dihydro-2H-indol-2-ylidene)penta-1,3-dienyl]-3H-indolium (Compound V);

Set 4
1-(6-{[2-(2,5-dioxo-2,5-dihydro-1H-pyrrol-1-yl)ethyl]amino}-6-oxohexyl)-2-[(1E,3E)-3-(3,3-dimethyl(1-sulpho-butyl)-1,3-dihydro-2H-indol-2-ylidene)prop-1-enyl]-3,3-dimethyl-3H-indolium (Compound VI); and
1-(5-{[2-(2,5-dioxo-2,5-dihydro-1H-pyrrol-1-yl)ethyl]amino}-6-oxopentyl)-3,3-dimethyl-2-[(1E,3E,5E)-5-(3,3-dimethyl-(1-sulpho-butyl)-1,3-dihydro-2H-indol-2-ylidene)penta-1,3-dienyl]-3H-indolium (Compound VII).

Set 5
1-(6-{[3-(2,5-dioxo-2,5-dihydro-1H-pyrrol-1-yl)propyl]amino}-6-oxohexyl)-2-[(1E,3E)-3-(1-ethyl-3,3-dimethyl-5-sulpho-1,3-dihydro-2H-indol-2-ylidene)prop-1-enyl]-3,3-dimethyl-3H-indolium (Compound VIII); and
1-(6-{[2-(2,5-dioxo-2,5-dihydro-1H-pyrrol-1-yl)ethyl]amino}-6-oxohexyl)-3,3-dimethyl-2-[(1E,3E,5E)-5-(1-ethyl-3,3-trimethyl-5-sulpho-1,3-dihydro-2H-indol-2-ylidene)penta-1,3-dienyl]-3H-indolium (Compound IV); and Set 6
1-(6-{[3-(2,5-dioxo-2,5-dihydro-1H-pyrrol-1-yl)propyl]amino}-6-oxohexyl)-2-[(1E,3E)-3-(3,3-dimethyl(1-sulpho-butyl)-1,3-dihydro-2H-indol-2-ylidene)prop-1-enyl]-3,3-dimethyl-3H-indolium (Compound IX); and
1-(6-{[2-(2,5-dioxo-2,5-dihydro-1H-pyrrol-1-yl)ethyl]amino}-6-oxohexyl)-3,3-dimethyl-2-[(1E,3E,5E)-5-(3,3-dimethyl-(1-sulpho-butyl)-1,3-dihydro-2H-indol-2-ylidene)penta-1,3-dienyl]-3H-indolium (Compound X).

The present invention therefore provides a matched set of reagents for reproducibly labelling all cysteine residues accessible in a mixture of cysteine-containing proteins under the conditions used. Equivalent migration in the pI dimension is achieved using dye sets with an overall neutral charge in order to match the neutral charge on the thiol group to which the dyes are conjugated. Neutral cyanine dyes may be obtained by means of a sulphonic acid or sulphonate group substituent covalently attached to the dye structure. Moreover, it has been discovered that equivalent mass migration is not simply achieved by matching the molecular weight of the dye sets, but rather, requires careful manipulation of the overall size and mass of the dye in order to achieve positional matching of proteins labelled with such dyes. In order to obtain equivalent migration employing a cysteine saturation labelling approach, dye sets are required wherein each of the matched dyes according to formula (I) differs in mass by a single carbon unit. The dye sets may be obtained by varying different substituents attached to the dye chromophore. Two or more spectrally resolved dyes that meet these criteria represent a matched saturation dye set.

The present invention also provides a method for saturation labelling of a protein with a fluorescent dye so as to label all available target amino acid residues in the protein, thereby giving essentially a single population of labelled protein molecules. Suitably, the target amino acid is a cysteine residue.

By the term "available" it is meant amino acid residues that are accessible to the fluorescent dye for reaction. Available cysteine residues must be accessible, and in a reduced (i.e. in a free thiol) form.

Thus, in a second aspect, there is provided a method for labelling a mixture of proteins in a sample wherein each of said proteins contains one or more cysteine residues, said method comprising:
i) adding to an aqueous liquid containing said sample a fluorescent dye wherein said dye contains a target bonding group that is covalently reactive with said proteins; and
ii) reacting said dye with said proteins so that said dye labels said proteins;
characterised in that all available cysteine residues in said proteins are labelled with said dye.

Preferably, the fluorescent dye according to the method of the second aspect is a cyanine dye. Particularly preferred cyanine dyes for use in the method are those containing a sulphonic acid or sulphonate group, for example, the dyes according to formula (I).

Preferably, the target bonding group is selected from a maleimido group and an iodoacetamido group.

In a preferred embodiment according to the second aspect, the method further comprises prior to step i), the step of treating the protein with a reductant.

Preferably, the cyanine dye is used in a range of 5 to 200 nmol of dye per 50 μg of protein.

Preferably, the method for labelling a mixture of proteins in a sample according to the second aspect is performed at a pH in the range 6.0 to 9.0.

The invention also provides a method for labelling and thereby imparting fluorescent properties to a sample, suitably a protein sample, using a dye according to formula (I). Thus, in a third aspect, there is provided a method for labelling one or more proteins in a sample, the method comprising:
i) adding to a liquid sample containing said one or more proteins a fluorescent dye of formula (I):

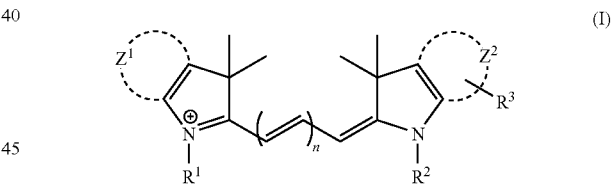

(I)

wherein n is different for each said dye and is 1, 2, or 3;
$Z^1$ and $Z^2$ independently represent the carbon atoms necessary to complete a phenyl or naphthyl ring system;
one of groups $R^1$ and $R^2$ is the group:

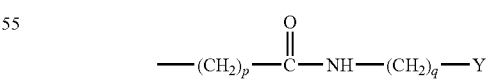

where Y is a target bonding group;
remaining group $R^1$ or $R^2$ is selected from —$(CH_2)_4$—W or —$(CH_2)_r$—H;
group $R^3$ is hydrogen, except when either $R^1$ or $R^2$ is —$(CH_2)_r$—H, in which case $R^3$ is W;
W is selected from sulphonic acid and sulphonate;
p is an integer from 3 to 6;
q is selected to be 2 or 3; and r is an integer from 1 to 5;
and their salts;
characterised in that when n of two of said dyes differs by +1, one of p, q and r of said two dyes differs by −1; and
incubating said dye with said sample under conditions suitable for labelling said one or more proteins.

Preferably, each of $Z^1$ and $Z^2$ represents the carbon atoms necessary to complete a phenyl ring system.

Preferably, the method according to the third aspect employs a fluorescent dye of formula (I) in which:
n is selected to be 1 or 2;
p is selected to be 4 or 5;
q is selected to be 2 or 3; and
r is selected to be 1, 2 or 3.

Preferably, the target bonding group Y is selected from a maleimido group and an iodoacetamido group.

To perform the method for saturation labelling of cysteine residues in proteins, a number of reaction parameters must be considered, including:

i) Accessibility of Protein Thiol Groups

In native folded proteins many cysteine residues are involved in the secondary structure of proteins by disulphide bond formation and may also be buried within the core of the molecule. In order to label these residues the protein must be unfolded to enable accessibility of the dyes, using protein denaturants such as urea, and they must be reduced to generate the free thiol. The choice of reductant is important to enable efficient reduction of the protein. Commonly used thiol-containing protein reductants are dithiothreitol (DTT) and β-mercaptoethanol. Suitable phosphine reductants include tributyl phosphine (TBP) and tris(2-carboxyethyl) phosphine (TCEP). Sodium borohydride may also be used. TCEP is a preferred reductant to give efficient reduction, whilst minimising reaction with the dye.

The efficiency of reduction is influenced by the concentration of reductant (relative to the cysteine content of protein sample), the temperature of reaction (which influences protein denaturation) and the duration of the reaction. If the reductant is immobilised on beads this may also affect the efficiency. The optimal reductant concentration for a particular sample type will vary depending on the reductant used and the cysteine content of the sample. However, 50 μg of protein typically requires 10 nmol of TCEP for reduction (assuming average cysteine content at 2%). For mammalian samples with higher cysteine content, then 20 nmol of TCEP is typically used. It is also important to maintain the ratio of 1 nmol TCEP to 2 nmol dye to give optimal labelling.

The optimum combination of these factors varies depending on the individual protein structure and cysteine content. Higher reduction temperature will give increased labelling, as a result of increased denaturation of the protein and thus increased accessibility of cysteines. However, high temperatures may have an adverse effect on the protein. Urea exists in equilibrium with carbamylate, but at higher temperatures (generally >40° C.) the equilibrium shifts in favour of the carbamylate. Carbamylate is a more chemically reactive species than urea and can attack primary amines (eg. N-terminal amino group and ϵ-amino group of lysines), leading to artefactual charge heterogeneity and the generation of charge trains on 2D gels. Saturation labelling of cysteine residues at 37° C. in the presence of urea does not exhibit carbamylation effects.

ii) Dye Concentration

The hydrophobic nature of the cyanine dyes requires the use of organic solvents (eg. 10% DMF) to aid solubility. To achieve saturation of the available target residues so that the labelling goes to completion it is necessary to use high concentrations of dye for labelling, whilst maintaining dye solubility. The use of a sulphonate group on the cyanine dyes helps to maintain solubility at high dye concentrations. The optimal dye concentration in the labelling reaction for a particular sample type will vary depending on the cysteine content of the sample and whether there are any other components in the sample which might interfere with labelling. However, the dye should always be present at least in excess of the thiol content to achieve saturation labelling and it is also important to maintain the ratio of 1 nmol TCEP to 2 nmol dye to give optimal labelling. Using the dye in excess would typically require the dye to be in the range 5 to 200 nmol per 50 μg of protein sample. However, 50 μg of protein typically requires 20 nmol of dye for a labelling reaction (assuming average cysteine content of 2%). For mammalian samples with higher cysteine content, 40 nmol of dye is typically used. However, other components in the sample may also react with the dye. For example, liver samples may contain elevated levels of the tripeptide glutathione, in response to stress/toxic substances. As a consequence, increased dye concentrations may be required in order to maintain labelling efficiency. Serum samples containing elevated levels of albumin, which is a highly abundant protein with a high cysteine content, may also require increased dye concentrations.

iii) pH of Labelling Reaction

Cysteine residues are strong nucleophiles and may be labelled in proteins using reagents having iodoacetamide and maleimide reactive groups. A particularly preferred reactive group is the maleimido group. The pKa of a thiol group is critical in determining its reactivity. Above the corresponding pH, its nucleophilicity increases markedly as the thiolate ($S^-$) form replaces the protonated SH species. In an isolated cysteine molecule, the thiol group has a pKa of approximately 8.6; however, the microenvironment of the thiol within the protein can also effect its pKa. The rate of reaction of thiol groups with maleimides increases at alkaline pH, due to the increased concentration of thiolate anion. Under alkaline conditions, hydrolysis of the maleimide to maleamic acid becomes a significant side reaction, and competing reactions with other functional groups such as lysine and histidine become more significant.

The ϵ-amino group of lysine behaves as a typical amine with a pKa in proteins of 9.0-9.5. At a lower pH, e.g. pH 6.5, the majority of amine groups are predominantly in the protonated, unreactive $NH_3^+$ form and the reaction with maleimide groups is ~1000 fold slower than with thiols. Terminal amine groups have pKa values of 7.5-8 depending on the amino acid concerned. The terminal amine will be present in the un-protonated (reactive) form at lower pH than those of lysine. Thus, reaction of maleimide groups with amines requires a higher pH than the reaction with thiol groups. Consequently, labelling of thiol groups with maleimides is more specific at lower pH, with less potential to label lysine residues. Thus, the pH of the reaction is also a critical factor in achieving saturation labelling and for specific labelling of thiol groups. Preferably, saturation labelling using fluorescent dyes, for example according to formula (I) is performed at a pH range of 6.0 to 9.0, most preferably a pH of 8.0, being a compromise between the presence of the reactive thiolate and the presence of reactive amines.

Protein samples for comparison may be derived from a variety of cell sources, including all normal and transformed cells derived from any recognised source with respect to species (eg. human, rodent, simian), tissue source (eg. brain, liver, lung, heart, kidney skin, muscle) and cell type (eg.

epithelial, endothelial). There are established protocols available for the culture of diverse cell types. (See for example, Freshney, R. I., Culture of Animal Cells: A Manual of Basic Technique, 2$^{nd}$ Edition, Alan R. Liss Inc. 1987). This invention may also be used to compare samples from plants using intact plants or cultured plant cells. In addition, samples for use in the method of the invention may be derived from cells which have been transfected with recombinant genes and cultured, cells which have been subjected to an external stimulus (such as heat shock or drug treatment) or other biological fluids (such as cerebrospinal fluid or serum). The present invention may also be used to target subsets of proteins present in a cell prior to labelling; for example, by isolating particular fractions such as low molecular weight proteins or pl range; sub-cellular compartments such as nuclear proteins.

Those skilled in the art will recognize that protein samples may be extracted from such samples using a variety of methods and extraction reagents. Typically, cells from the tissue/culture are disrupted, for example by homogenization, sonication, cell lysis, and the protein extracted and solubilised in the presence of reagents including denaturing reagents, such as urea, thiourea, detergents such as SDS, CHAPS, Triton X-100, NP-40, reducing agents, such as dithiothreitol (DTT), mercaptoethanol, and buffer such as Tris, Hepes. Protease inhibitors, such as phenylmethanesulphonyl fluoride (PMSF), ethylenediaminetetraacetic acid (EDTA), leupeptin, aprotinin, may also be added to minimise degradation by endogenous proteases.

The matched set of fluorescent dyes and the labelling method may be used for detecting differences in the protein content of at least two different protein samples, for example, according to the method described by Minden, J. et al (Electrophoresis, (1997), 18, 2071). In a typical example of the method, protein is extracted from each of 2 different samples by known methods as described above and the protein concentration determined. To a 50 μg aliquot of each protein extract is added 10 nmol of TCEP (tris-(2-carboxyethyl) phosphine) and this is incubated for one hour at 37° C. To each of these reduced protein samples is added 20 nmol of dye and incubated for 30 minutes at 37° C. The first protein sample is labelled with the first dye (for example Cy3) of a matched set of dyes and the second protein sample is labelled with the second dye of the matched set of dyes (for example Cy5). The reaction is stopped by the addition of sample buffer containing DTT. The labelled protein samples are mixed to give a single sample for separation. The samples are electrophoretically separated, preferably by 2D-PAGE. The procedures for electrophoretic separation are well known to those skilled in the art.

In a fourth aspect of the invention, a kit is provided, said kit comprising a matched set of fluorescent dyes comprising at least two different fluorescent dyes having the formula (I):

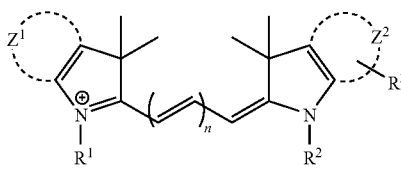

(I)

wherein n is different for each said dye and is 1, 2, or 3;
$Z^1$ and $Z^2$ independently represent the carbon atoms necessary to complete a phenyl or naphthyl ring system;
one of groups $R^1$ and $R^2$ is the group:

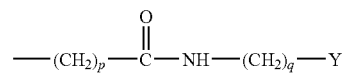

where Y is a target bonding group;
remaining group $R^1$ or $R^2$ is selected from —$(CH_2)_4$—W or —$(CH_2)_r$—H;
group $R^3$ is hydrogen, except when either $R^1$ or $R^2$ is —$(CH_2)_r$—H, in which case $R^3$ is W;
W is selected from sulphonic acid and sulphonate;
p is an integer from 3 to 6;
q is selected to be 2 or 3; and
r is an integer from 1 to 5;
and their salts;
characterised in that when n of two of said dyes differs by +1, one of p, q and r of said two dyes differs by −1.

BRIEF DESCRIPTION OF THE DRAWINGS

The invention is further illustrated by reference to the following examples and figures in which:

FIG. 2 shows overlay images of proteins labelled with dye sets 1, 12 and 9 and separated by 2D electrophoresis with outlines of labelled protein spots to demonstrate the positional matching.

Figure 1:
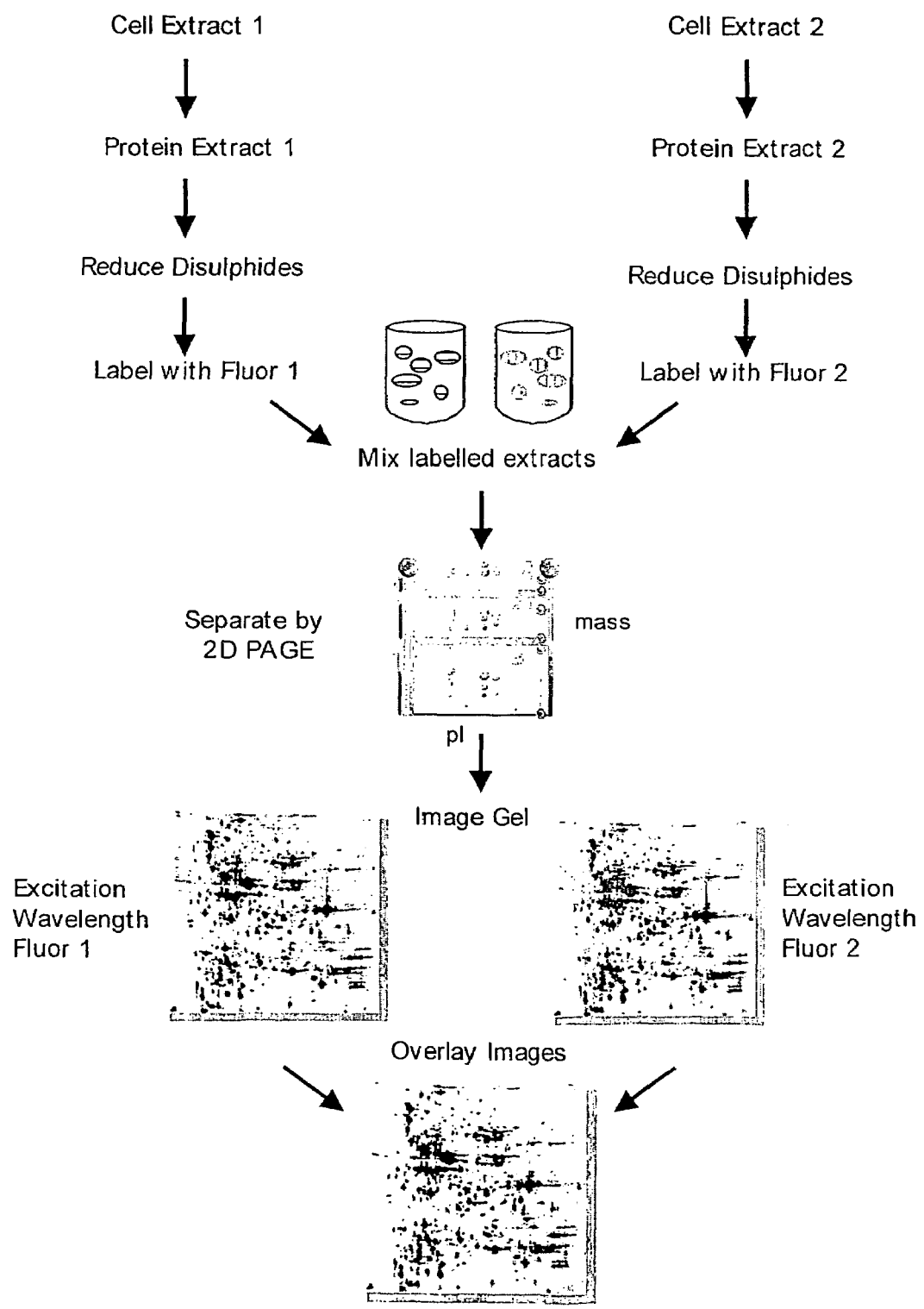
FIG. 1 illustrates a typical workflow for differential analysis of protein samples using cysteine reactive dyes with 2D electrophoresis. Two different protein samples are prepared from cells, tissues or other biological fluids. The first and second protein samples may be any two samples in which it is desired to compare the protein content, for example, from a normal and diseased tissue, or from control versus drug treated/stimulated cells. The method may also be applied to one dimensional separation systems.

The invention is further illustrated by reference to the following examples.

EXAMPLES

Example 1

Synthesis of Dyes i) General Experimental Procedures

1H NMR ($\delta_H$) spectra were recorded on a Jeol JNM-LA300 FT NMR spectrometer. Chemical shifts are reported in δ (ppm). Samples were prepared as solutions in a suitable deuterated solvent such as $d_4$-methanol. UV/VIS spectroscopy was conducted using the Unicam UV3 UV/VIS spectrometer. Trimethoxypropene was purchased from Karl Industries Inc., Ohio, USA. All other chemicals were purchased from Sigma-Aldrich Company Limited, Dorset, England.

N-BOC-Aminoethylmaleimide and N-BOC-aminopropylmaleimide were prepared according to the literature description in J. Org. Chem., (1995), 60, 5352-5355.

ii) Potassium 2,3,3-trimethylindolenine-5-sulphonic acid

Hydrazinobenzenesulphonic acid (20.0 g) was dissolved in acetic acid (60 ml) and 3-methyl-2-butanone (26.0 g) added then heated at reflux for 3 hours. The desired compound was precipitated by cooling in the fridge with scratching and the off white slurry was diluted with propan-2-ol and filtered (71%).

The 2,3,3-trimethyl-5-sulphonyl-indolenine (16.45 g) was dissolved in methanol (160 ml) with heating and a saturated solution of KOH in propan-2-ol (100 ml) was added. The solution changed to a yellow colour and a solid formed. The solution was cooled and the solid was filtered to form an off-white solid (15.9 g, 98%). $\delta_H$ (300 MHz, CD$_3$OD) 7.84 (m, 2H), 7.46 (d, 1H), 3.30 (s, 3H) and 1.35 (s, 6H).

iii) 1,2,3,3-Tetramethyl-5-sulphonyl-indolium iodide

Potassium 2,3,3-trimethylindolenine-5-sulphonic acid (1.0 g, 3.61 mmol) and iodomethane (0.25 ml, 3.97 mmol) were mixed with dichlorobenzene (10 ml) under a nitrogen atmosphere. The solution was heated at 100° C. using a sand bath for 4 hours. A solid had begun to form but analysis by tlc (30% MeOH/70% DCM) showed product formation was not complete so an additional equivalent of iodomethane was added and the reaction heated for an additional 2 hours before cooling to room temperature. The solid was collected by filtration, washed with dichlorobenzene, diethyl ether then dried in vacuo to afford a purple solid (0.89 g, 98%). $\delta_H$ (300 MHz, CD$_3$OD) 8.06 (m, 1H), 7.94 (dd, 1H), 7.84 (m, 1H), 4.02 (s, 3H) and 1.61 (s, 6H).

iv) 1-Ethyl-2,3,3-trimethyl-5-sulphonyl-indolium iodide

Potassium 2,3,3-trimethylindolenine-5-sulphonic acid (10.0 g, 41.97 mmol) and iodoethane (4.0 ml, 50.35 mmol) were mixed with dichlorobenzene (40 ml under a nitrogen atmosphere. The solution was heated at 120° C. using a sand bath for 16 hours producing a purple solid. The solid was collected by filtration then washed with dichlorobenzene, chloroform and ether to produce pale pink solid, (10.2 g, 91%). $\delta_H$ (300 MHz, CD$_3$OD) 7.98 (m, 3H), 4.55 (q, 2H), 1.56 (s, 6H) and 1.48 (t, 3H).

v) 1-Propyl-2,3,3-trimethyl-5-sulphonyl-indolium iodide

Potassium 2,3,3-trimethylindolenine-5-sulphonic acid (1.0 g, 3.61 mmol) and iodopropane (0.4 ml, 3.97 mmol) were mixed with dichlorobenzene (10 ml) under a nitrogen atmosphere. The solution was heated at 100° C. using a sand bath for 20 hours producing a red-brown colour gelatinous solid. The solid was collected by filtration and then washed with dichlorobenzene, chloroform and diethyl ether to afford a pink solid, (472 mg, 47%). $\delta_H$ (300 MHz, CD$_3$OD) 7.91 (m, 3H), 4.50 (t, 2H), 2.01 (dt, 2H), 1.56 (s, 6H) and 1.13 (t, 3H).

vi) 1-Sulphobutyl-2,3,3-trimethyl-5-sulphonyl-indolium iodide 2,3,3-Trimethylindolenine (2.0 g, 12.6 mmol) and 1,4-butanesultone (1.7 g, 12.6 mmol) were mixed together and heated at 100° C. for 6 hours. The solution gradually turned red and after the 6 hours the reaction was cooled to room temperature. The solid was dispersed in diethyl ether and filtered. The solid was collected and dried. $\delta_H$ (300 MHz, CD$_3$OD) 7.91 (m, 1H), 7.75 (m, 1H), 7.42 (m, 2H), 4.58 (m, 2H), 2.93 (m, 2H), 2.18 (m, 2H), 1.94 (m, 2H) and 1.61 (s, 6H).

vii) 1-(5-Carboxypentyl)-2,3,3-trimethyl-5-sulphonyl-indolium iodide 2,3,3-Trimethylindolenine (6.4 g, 40 mmol) was dissolved in dichlorobenzene (25 ml) and stirred until the solution was homogenous. To this was added 6-bromohexanoic acid (15.6 g, 80 mmol) and the reaction heated to 110° C. in a sand bath for 6.5 hours. The reaction was allowed to cool to room temperature where the sides of the flask were scratched then the flask was placed in the fridge for 1 hour. After this time, a beige solid had formed in the purple solution so the solid was collected by filtration then washed with dichlorobenzene and ether to afford a beige solid (7.42 g, 52%). $\delta_H$ (300 MHz, CD$_3$OD) 7.91 (m, 1H), 7.78 (m, 1H), 7.62 (m, 2H), 4.52 (t, 2H), 2.38 (t, 2H), 2.04 (p, 2H), 1.88-2.45 (m, 4H) and 1.61 (s, 6H).

viii) 1-(4-Carboxybutyl)-2,3,3-trimethyl-5-sulphonyl-indolium iodide 2,3,3-Trimethylindolenine (11.3 g, 40 mmol) was dissolved in dichlorobenzene (30 ml and stirred until the solution was homogenous. To this was added 5-bromobutanoic acid (19.3 g, 106.6 mmol) and the reaction heated to 110° C. in a sand bath for 6.5 hours. The reaction was allowed to cool to room temperature where the sides of the flask were scratched then the flask was placed in the fridge for 1 hour. After this time a beige solid had formed in the purple solution so the solid was collected by filtration then washed with dichlorobenzene and ether to afford a beige solid (18.0 g, 75%). $\delta_H$ (300 MHz, CD$_3$OD) 7.90 (m, 1H), 7.78 (m, 1H), 7.62 (m, 2H), 4.59 (t, 2H), 2.41 (t, 2H), 2.04 (m, 2H), 1.76 (m, 2H) and 1.61 (s, 6H).

ix) Aminoethylmaleimide and Aminopropylmaleimide

To a solution of 4M hydrochloric acid in dioxane was added the appropriate BOC-aminoalkylmaleimide and the reaction stirred at room temperature for 30 minutes. After this time the reaction had deposited a solid and the solvents were removed in vacuo to reveal a white fluffy solid. The compound was used crude in subsequent steps.

x) 1-(6-{[2-(2,5-Dioxo-2,5-dihydro-1H-pyrrol-1-yl)ethyl]amino}-6-oxohexyl)-2-[(1E,3E)-3-(1-ethyl-3,3-dimethyl-5-sulpho-1,3-dihydro-2H-indol-2-ylidene)prop-1-enyl]-3,3-dimethyl-3H-indolium (Compound I)

1-Ethyl-2,3,3-trimethyl-5-sulphonyl-indolium iodide (2.0 g, 7.48 mmol), N,N'-diphenylformamidine (1.5 g, 7.48 mmol) and triethylorthoformate (1.1 g, 7.48 mmol) were dissolved in ethanol (10 ml) then heated at reflux (100° C.) for 3 hours. A solid formed on the sides of the reaction flask and UV/VIS showed a new peak at 408 nm. Diethyl ether was added and the precipitate and the solid collected by filtration, washed with ether and dried in vacuo to afford a yellow/orange solid (1.83 g, 66%). UV/VIS (MeOH); absorption $\lambda_{max}$=408 nm.

To a solution of the Cy3 half-dye (1.83 g, 6.22 mmol) in anhydrous pyridine (10 ml) was added acetic anhydride (1.0 ml) and the reaction stirred under a nitrogen atmosphere for 10 minutes. After this time 1-(5-carboxypentyl)-2,3,3-trimethyl indolium bromide (2.2 g, 6.22 mmol) was added and the reaction stirred at room temperature for 16 hours. The progress of the reaction was monitored by tlc (20% MeOH/

80% DCM). The solvent was removed under reduced pressure and purified using flash column chromatography (reversed phase silica: water-50% methanol gradient) to yield 299 mg of the desired Cy3 acid product (9%). UV/VIS (MeOH); absorption $\lambda_{max}$=550 nm.

Cy3 acid (200 mg, 0.36 mmol) was dissolved in anhydrous DMF under a nitrogen atmosphere then stirred at room temperature. DIPEA (80 µl, 0.40 mmol) and TSTU (120 mg, 0.40 mmol) were added and the reaction stirred for 2 hours until deemed complete to the NHS ester by tlc (20% MeOH/80% DCM). The NHS ester was treated with a second equivalent of DIPEA (80 µl, 0.40 mmol) and aminoethyimaleimide (80 mg, 0.40 mmol) were added and the reaction allowed to stir for 2 hours. Thin layer chromatography (Tlc) showed conversion to a new product so the reaction was diluted with diethyl ether (50 ml) and the solvents decanted to leave a pink residue. Flash column chromatography (silica: DCM-40% methanol gradient) afforded the desired maleimide product (98 mg, 34%). UV/VIS (MeOH); absorption $\lambda_{max}$=550 nm. $\delta_H$ (300 MHz, CD$_3$OD) 8.56 (t, 1H), 7.92 (m, 2H), 7.62-7.38 (m, 5H), 6.72 (s, 2H), 6.50 (dd, 2H), 4.19 (m, 4H), 3.52 (m, 2H), 2.15 (t, 2H), 1.94-1.56 (m, 6H), 1.75 (s, 12H) and 1.44 (t, 3H).

xi) 1-(6-{[2-(2,5-Dioxo-2,5-dihydro-1H-pyrrol-1-yl)ethyl]amino}-6-oxohexyl)-3,3-dimethyl-2-[(1E,3E,5E)-5-(1,3,3-trimethyl-5-sulpho-1,3-dihydro-2H-indol-2-ylidene)penta-1,3-dienyl]-3H-indolium (Compound II)

1,2,3,3-Tetramethyl-5-sulphonyl-indolium iodide (5.00 g, 11.90 mmol) was suspended in a mixture of acetic acid (40 ml) and TFA (2 ml, 18.0 mmol) until all of the solid dissolved. 1,3,3-Trimethoxypropene (12.5 ml, 95.0 mmol) was added to the reaction and stirred at room temperature for 5 hours. The solution was pipetted into 500 ml of diethyl ether and the precipitate collected by filtration (4.80 g, contains salts).

To a solution of the Cy5 half-dye (4.80 g, 14.9 mmol) in methanol (40 ml was added potassium acetate (3.00 g, 34.2 mmol) and 1-(5-carboxypentyl)-2,3,3-trimethyl indolium bromide (3.00 g, 16.4 mmol). After stirring overnight, the solution was pipetted into diethyl ether (500 ml) and the blue solid collected by filtration and dried in vacuo. Purification was achieved by flash column chromatography (reversed phase silica: water-50% methanol gradient) to yield 2.30 g of desired product (28%). UV/VIS (MeOH); absorption $\lambda_{max}$=642 nm.

Cy5 acid (200 mg, 0.36 mmol) was dissolved in anhydrous DMF under a nitrogen atmosphere then stirred at room temperature. DIPEA (80 µl, 0.40 mmol) and TSTU (120 mg, 0.40 mmol) were added and the reaction stirred for 2 hours until deemed complete to the NHS ester by tlc (20% MeOH/80% DCM). The NHS ester was treated with a second equivalent of DIPEA (80 µl, 0.40 mmol) and aminoethylmaleimide (80 mg, 0.40 mmol) were added and the reaction allowed to stir for 2 hours. Tlc showed conversion to a new product so the reaction was diluted with diethyl ether (50 ml) and the solvents decanted to leave a blue residue. Flash column chromatography (silica: DCM-40% methanol gradient) afforded the desired maleimide product (105 mg, 43%). UV/VIS (MeOH); absorption $\lambda_{max}$=644 nm. $\delta_H$ (300 MHz, CD$_3$OD) 8.18 (dt, 2H), 7.82 (m, 2H), 7.56-7.24 (m, 5H), 6.80 (s, 2H), 6.64 (t, 1H), 6.45 (d, 1H), 6.24 (d, 1H), 4.17 (t, 2H), 3.60 (s, 3H), 3.40 (t, 2H), 2.09 (t, 2H), 1.89-1.48 (m, 6H) and 1.79 (s, 12H).

xii) 1-(6-{[2-(2,5-Dioxo-2,5-dihydro-1H-pyrrol-1-yl)ethyl]amino}-6-oxohexyl)-2-[(1E,3E)-3-(1-propyl-3,3-dimethyl-5-sulpho-1,3-dihydro-2H-indol-2-ylidene)prop-1-enyl]-3,3-dimethyl-3H-indolium (Compound III)

1-(5-Carboxypentyl)-2,3,3-trimethyl-5-sulphonyl-indolium (6.0 g, 16.94 mmol) and N,N'-diphenylformamidine (6.63 g, 33.87 mmol were dissolved in acetic acid (20 ml) then heated at reflux (120° C.) for 4 hours. The reaction was allowed to cool to room temperature then the solvents removed in vacuo. The orange oil was dissolved in chloroform and washed with water then dried with magnesium sulphate and concentrated to an orange oil of the Cy3 half-dye. This oil was used without further purification.

To a solution of the Cy3 half-dye (1.00 g, 2.18 mmol) in anhydrous pyridine (10 ml) was added acetic anhydride (1.0 ml) and the reaction stirred under a nitrogen atmosphere for 10 minutes. After this, 1-propyl-2,3,3-trimethyl-5-sulphonyl-indolium iodide (0.92 g, 3.28 mmol) was added and the reaction stirred at room temperature for 16 hours. The progress of the reaction was monitored by tlc (20% MeOH/80% DCM). The solvent was removed under reduced pressure and purified using flash column chromatography (silica: DCM-40% methanol gradient) to yield 241 mg of the desired Cy3 acid product (21%). UV/VIS (MeOH); absorption $\lambda_{max}$=550 nm.

Cy3 acid (100 mg, 0.18 mmol) was dissolved in anhydrous DMF under a nitrogen atmosphere then stirred at room temperature. DIPEA (30 µl, 0.20 mmol) and TSTU (54 mg, 0.20 mmol) were added and the reaction stirred for 2 hours until deemed complete to the NHS ester by tlc (20% MeOH/80% DCM). The NHS ester was treated with a second equivalent of DIPEA (30 µl, 0.20 mmol) and aminoethylmaleimide (40 mg, 0.20 mmol) were added and the reaction allowed to stir for 2 hours. Tlc showed conversion to a new product so the reaction was diluted with diethyl ether (50 ml) and the solvents decanted to leave a pink residue. Flash column chromatography (silica: DCM-40% methanol gradient) afforded the desired maleimide product (41 mg, 34%). UV/VIS (MeOH); absorption $\lambda_{max}$=550 nm. $\delta_H$ (300 MHz, CD$_3$OD) 8.52 (t, 1H), 7.90 (m, 2H), 7.60-7.39 (m, 5H), 6.78 (s, 2H), 6.52 (dd, 2H), 4.22 (m, 4H), 3.56 (m, 2H), 2.13 (t, 2H), 1.97-1.56 (m, 8H), 1.75 (s, 12H) and 1.09 (t, 3H).

xiii) 1-(6-{[2-(2,5-Dioxo-2,5-dihydro-1H-pyrrol-1-yl)ethyl]amino}-6-oxohexyl)-3,3-dimethyl-2-[(1E,3E,5E)-5-(1-ethyl-3,3-trimethyl-5-sulpho-1,3-dihydro-2H-indol-2-ylidene)penta-1,3-dienyl]-3H-indolium (Compound IV)

1-(5-Carboxypentyl)-2,3,3-trimethyl-5-sulphonyl-indolium (4.0 g, 14.59 mmol) and malonaldehyde bis(phenylimine)hydrochloride (7.55 g, 29.18 mmol) were dissolved in acetic acid (20 ml then heated at reflux (120° C.) for 4 hours. The reaction was allowed to cool to room temperature then the solvents removed in vacuo. The red oil was dissolved in chloroform and washed with water then dried with magnesium sulphate and concentrated to a red oil of the Cy5 half-dye. This oil was used without further purification.

To a solution of the Cy5 half-dye (1.00 g, 2.07 mmol) in anhydrous pyridine (10 ml) was added acetic anhydride (1.0 ml) and the reaction stirred under a nitrogen atmosphere for 10 minutes. To this 1-ethyl-2,3,3-trimethyl-5-sulphonyl-indolium iodide (0.59 g, 2.28 mmol) was added and the reaction stirred at room temperature for 16 hours. The progress of the reaction was monitored by tlc (20% MeOH/80% DCM). The solvent was removed under reduced pressure and purified using flash column chromatography (silica: DCM-40% methanol gradient) to yield 365 mg of the desired Cy5 acid product (31%). UV/VIS (MeOH); absorption $\lambda_{max}$=644 nm.

Cy5 acid (52 mg, 0.09 mmol) was dissolved in anhydrous DMF under a nitrogen atmosphere then stirred at room temperature. DIPEA (10 μl, 0.10 mmol) and TSTU (28 mg, 0.10 mmol) were added and the reaction stirred for 2 hours until deemed complete to the NHS ester by tlc (20% MeOH/80% DCM). The NHS ester was treated with a second equivalent of DIPEA (10 μl, 0.10 mmol) and aminoethylmaleimide (18 mg, 0.10 mmol) were added and the reaction allowed to stir for 2 hours. Tlc showed conversion to a new product so the reaction was diluted with diethyl ether (30 ml and the solvents decanted to leave a blue residue. Flash column chromatography (silica: DCM-40% methanol gradient) afforded the desired maleimide product (29 mg, 47%). UV/VIS (MeOH); absorption $\lambda_{max}$=644 nm. $\delta_H$ (300 MHz, CD$_3$OD) 8.38 (m, 2H), 7.88 (m, 2H), 7.55-7.24 (m, 5H), 6.80 (s, 2H), 6.71 (t, 1H), 6.42 (d, 1H), 6.24 (d, 1H), 4.11 (m, 4H), 3.54 (t, 2H), 2.12 (t, 2H), 1.92-1.36 (m, 9H) and 1.81 (s, 12H).

xiv) 1-(5-{[2-(2,5-Dioxo-2,5-dihydro-1H-pyrrol-1-yl)ethyl]amino}-6-oxopentyl)-3,3-dimethyl-2-[(1E,3E,5E)-5-(1-ethyl-3,3-trimethyl-5-sulpho-1,3-dihydro-2H-indol-2-ylidene)penta-1,3-dienyl]-3H-indolium (Compound V)

1-(4-Carboxybutyl)-2,3,3-trimethyl indolium bromide (2.00 g, 5.88 mmol) and malonaldehyde bis(phenylimine) hydrochloride (2.28 g, 8.82 mmol) were dissolved in acetic acid (30 ml) then heated at 120° C. for 6 hours. The reaction was then allowed to cool before the acetic acid was removed in vacuo afford a mobile oil. This was dissolved in chloroform and washed with water, dried with magnesium sulphate, filtered and concentrated in vacuo to afford a more viscous oil. Most of the unreacted malonaldehyde bis(phenylimine) remained at the interface of the chloroform/ water. The compound was purified using flash column chromatography (dichloromethane-30% methanol gradient) to afford a red solid (120 mg, 5%).

To a solution of the Cy5 half-dye (120 mg, 0.31 mmol) in anhydrous pyridine (3 ml) was added acetic anhydride (0.5 ml) and the reaction stirred under a nitrogen atmosphere for 10 minutes. After this time, the 1-ethyl-2,3,3-trimethyl-5-sulphonyl-indolium iodide (83 mg, 0.31 mmol) was added and the reaction stirred at room temperature overnight. The solvent was removed under reduced pressure and purified using flash column chromatography (silica: dichloromethane-40% methanol gradient) to yield 84 mg of desired product (48%). UV/VIS (MeOH); absorption $\lambda_{max}$=644 nm.

Cy5 (84 mg, 0.15 mmol) was dissolved in anhydrous DMF under a nitrogen atmosphere then stirred at room temperature. DIPEA (26 μl, 0.15 mmol) and TSTU (45 mg, 0.15 mmol) were added and the reaction stirred for 2 hours until deemed complete to the NHS ester by tlc (20% MeOH/80% DCM). The NHS ester was treated with a second equivalent of DIPEA (DIPEA (26μl, 0.15 mmol) and then aminoethylmaleimide (52 mg, 0.30 mmol) was added and the reaction allowed to stir for an additional 2 hours. Tlc showed conversion to a new product, so the reaction was diluted with diethyl ether (50 ml) and the solvents decanted to leave a pink residue. Flash column chromatography (silica: DCM-40% methanol gradient) afforded the desired maleimide product (30 mg, 30%). UV/VIS (MeOH); absorption $\lambda_{max}$=644 nm. $\delta_H$ (300 MHz, CD$_3$OD) 8.15 (q, 2H), 7.80 (m, 2H), 7.52-7.31 (m, 5H), 6.75 (s, 2H), 6.64 (t, 1H), 6.46 (d, 1H), 6.32 (d, 1H), 4.27 (m, 4H), 4.15 (t, 2H), 2.09 (t, 2H), 1.79 (s, 6H), 1.65 (s, 6H) 2.56-2.44 (m, 4H) and 1.12 (t, 3H).

xv) 1-(6-{[2-(2,5-Dioxo-2,5-dihydro-1H-pyrrol-1-yl)ethyl]amino}-6-oxohexyl)-2-[(1E,3E)-3-(3,3-dimethyl(1-sulpho-butyl)-1,3-dihydro-2H-indol-2-ylidene)prop-1-enyl]-3,3-dimethyl-3H-indolium (Compound VI)

1-(5-Carboxypentyl)-2,3,3-trimethyl indolium bromide (500 mg, 1.41 mmol), N,N'-diphenylformamidine (278 mg, 1.41 mmol) and 1-sulphobutyl-2,3,3-trimethylindolium iodide (418 mg, 1.41 mmol) were dissolved in anhydrous pyridine (5 ml) and stirred at room temperature. Acetic anhydride (0.4 ml) was then added and the reaction stirred overnight at ambient temperature. The pyridine was removed in vacuo and the magenta oil purified by flash column chromatography (dichloromethane-10% methanol gradient) to afford a pink solid (67 mg, 8%).

The Cy3 acid (50 mg, 0.09 mmol) was dissolved in anhydrous DMF under a nitrogen atmosphere then stirred at room temperature. DIPEA (20 μl, 0.09 mmol) and TSTU (59 mg, 0.18 mmol) were added and the reaction stirred for 2 hours until deemed complete to the NHS ester by tlc (20% MeOH/80% DCM). The NHS ester was treated with a second equivalent of DIPEA (20 μl, 0.09 mmol) and then the aminoethylmaleimide (32 mg, 0.18 mmol) was added and the reaction allowed to stir for an additional 2 hours. The reaction was diluted with diethyl ether (50 ml) and the solvents decanted to leave a pink residue. Flash column chromatography (silica: DCM-40% methanol gradient) afforded the desired maleimide product (24 mg, 43%). UV/VIS (MeOH); absorption $\lambda_{max}$=550 nm. $\delta_H$ (300 MHz, CD$_3$OD) 8.49 (t, 1H), 7.52-7.35 (m, 8H), 6.72 (s, 2H), 6.46 (dd, 2H), 4.09 (m, 4H), 3.57 (m, 2H), 2.85 (m, 2H), 2.15 (t, 2H), 1.94-1.43 (m, 10H) and 1.85 (s, 12H).

xvi) 1-(5-{[2-(2,5-Dioxo-2,5-dihydro-1H-pyrrol-1-yl)ethyl]amino}-6-oxopentyl)-3,3-dimethyl-2-[(1E,3E,5E)-5-(3,3-dimethyl-(1-sulpho-butyl)-1,3-dihydro-2H-indol-2-ylidene)penta-1,3-dienyl]-3H-indolium (Compound VII)

1-(4-Carboxybutyl)-2,3,3-trimethyl indolium bromide (1.0 g, 2.94 mmol) and malonaldehyde bisphenylimine hydrochloride (760 mg, 2.94 mmol) were dissolved in acetic acid (10 ml) then heated at 120° C. for 18 hours. The reaction was then allowed to cool before the acetic acid was removed in vacuo afford a mobile red oil. This was dissolved in chloroform and washed with water, dried with magnesium sulphate, filtered and concentrated in vacuo to afford a more viscous red/brown oil. The compound was purified using flash column chromatography (dichloromethane-20% methanol gradient) to afford an orange solid (1.43 g, 55%).

To a solution of the Cy5 half-dye (120 mg, 0.26 mmol) in anhydrous pyridine (5 ml) was added acetic anhydride (0.5 ml and the reaction stirred under a nitrogen atmosphere for 10 minutes. After this time 1-sulphobutyl-2,3,3-trimethylindolium iodide (83 mg, 0.28 mmol) was added and the reaction stirred at room temperature for 2 hours. The solvent was removed under reduced pressure and purified using flash column chromatography (silica: dichloromethane-20% methanol gradient) to yield 78 mg of desired product (51%).

The Cy5 acid (50 mg, 0.09 mmol) was dissolved in anhydrous DMF under a nitrogen atmosphere then stirred at room temperature. DIPEA (15 μl, 0.10 mmol) and TSTU (28 mg, 0.10 mmol) were added and the reaction stirred for 2 hours until deemed complete to the NHS ester by tlc (20% MeOH/ 80% DCM). The NHS ester was treated with a second equivalent of DIPEA (15 µl, 0.10 mmol) and then aminoethylmaleimide (30 mg, 0.17 mmol) was added and the reaction allowed to stir for an additional 2 hours. Tlc analysis showed conversion to a new product. The reaction was diluted with diethyl ether (50 ml) and the solvents decanted to leave a blue residue. Flash column chromatography (silica: DCM-40% methanol gradient) afforded the desired maleimide product (30 mg, 30%). UV/VIS (MeOH); absorption $\lambda_{max}$=644 nm. $\delta_H$ (300 MHz, CD$_3$OD) 8.19 (t, 2H), 7.52-7.42 (m, 8H), 6.71 (s, 2H), 6.64 (t, 1H), 6.36 (dt, 2H), 4.18 (m, 4H), 3.55 (m, 2H), 2.89 (m, 2H), 2.15 (t, 2H), 1.79 (s, 12H) and 2.01-1.36 (t, 8H).

xvii) 1-(6-{[3-(2,5-Dioxo-2,5-dihydro-1H-pyrrol-1-yl)propyl]amino}-6-oxohexyl)-2-[(1E,3E)-3-(1-ethyl-3,3-dimethyl-5-sulpho-1,3-dihydro-2H-indol-2-ylidene)prop-1-enyl]-3,3-dimethyl-3H-indolium (Compound VIII)

1-(5-Carboxypentyl)-2,3,3-trimethyl indolium bromide (354 mg, 1.00 mmol), N,N'-diphenylformamidine (196 mg, 1.00 mmol) and 1-ethyl-2,3,3-trimethyl-5-sulphonyl-indolium iodide (267 mg, 1.00 mmol) were dissolved in anhydrous pyridine (15 ml) and stirred at room temperature. Acetic anhydride (0.5 ml) was then added and the reaction stirred overnight at ambient temperature. The pyridine was removed in vacuo and the magenta oil purified by flash column chromatography (dichloromethane-40% methanol gradient) to afford a pink solid (30 mg, 6%).

The Cy3 acid (30 mg, 0.05 mmol) was dissolved in anhydrous DMF under a nitrogen atmosphere then stirred at room temperature. DIPEA (10 µl, 0.05 mmol) and TSTU (2 mg, 0.05 mmol) were added and the reaction stirred for 2 hours until deemed complete to the NHS ester by tlc (20% MeOH/ 80% DCM). The NHS ester was treated with a second equivalent of DIPEA (10 µl, 0.05 mmol) and then the aminoethylmaleimide (9 mg, 0.05 mmol) was added and the reaction allowed to stir for an additional 2 hours. The reaction was diluted with diethyl ether (20 ml and the solvents decanted to leave a pink residue. Flash column chromatography (silica: DCM-40% methanol gradient) afforded the desired maleimide product (15 mg, 44%). UV/VIS (MeOH); absorption $\lambda_{max}$=550 nm. $\delta_H$ (300 MHz, CD$_3$OD) 8.53 (t, 1H), 7.95 (m, 2H), 7.59-7.41 (m, 5H), 6.78 (s, 2H), 6.50 (t, 2H), 4.17 (m, 4H), 3.50 (m, 2H), 3.14 (t, 2H), 2.14 (t, 2H), 1.98-1.28 (m, 11H) and 1.79 (s, 12H).

xviii) 1-(6-{[3-(2,5-Dioxo-2,5-dihydro-1H-pyrrol-1-yl)propyl]amino}-6-oxohexyl)-2-[(1E,3E)-3-(3,3-dimethyl(1-sulpho-butyl)-1,3-dihydro-2H-indol-2-ylidene)prop-1-enyl]-3,3-dimethyl-3H-indolium (Compound IX)

1-(5-Carboxypentyl)-2,3,3-trimethyl indolium bromide (6.0 g, 16.95 mmol) and N,N'-diphenylformamidine (6.63 g, 33.87 mmol) were dissolved in acetic acid (20 ml) then heated at 120° C. for 5 hours. The acetic acid was removed in vacuo and the residue purified using column chromatography (silica: dichloromethane-20% methanol gradient) yellow/orange solid (1.34 g, 21%).

To a solution of the Cy3 half-dye (250 mg, 0.55 mmol) in anhydrous pyridine (5 ml) was added acetic anhydride (0.5 ml) and the reaction stirred under a nitrogen atmosphere for 10 minutes. After this time 1-sulphobutyl-2,3,3-trimethylindolium iodide (161 mg, 0.55 mmol) was added and the reaction stirred at room temperature for 22 hours. The solvent was removed under reduced pressure and purified using flash column chromatography (silica: dichloromethane-20% methanol gradient) to yield 142 mg of the desired Cy3 acid product (45%).

Cy3 acid (50 mg, 0.09 mmol) was dissolved in anhydrous DMF under a nitrogen atmosphere then stirred at room temperature. DIPEA (15 µl, 0.10 mmol) and TSTU (28 mg, 0.10 mmol) were added and the reaction stirred for 2 hours until deemed complete to the NHS ester by tlc (20% MeOH/80% DCM). The NHS ester was treated with a second equivalent of DIPEA (15 µl, 0.10 mmol) and aminopropylmaleimide (18 mg, 0.10 mmol) were added and the reaction allowed to stir for 2 hours. The reaction was diluted with diethyl ether (50 ml) and the solvents decanted to leave a pink residue. Flash column chromatography (silica: DCM-40% methanol gradient) afforded the desired maleimide product (15 mg, 24%). $\delta_H$ (300 MHz, CD$_3$OD) 8.49 (t, 1H), 7.78-7.22 (m, 8H), 6.72 (s, 2H), 6.50 (t, 2H), 4.12 (m, 4H), 3.47 (m, 2H), 3.10 (m, 2H), 2.85 (m, 2H), 2.15 (t, 2H), 2.01-1.24 (m, 12H) and 1.85 (s, 12H).

xix) 1-(6-{[2-(2,5-Dioxo-2,5-dihydro-1H-pyrrol-1-yl)ethyl]amino}-6-oxohexyl)-3,3-dimethyl-2-[(1E,3E,5E)-5-(3,3-dimethyl-(1-sulpho-butyl)-1,3-dihydro-2H-indol-2-ylidene)penta-1,3-dienyl]-3H-indolium (Compound X)

1-(5-Carboxypentyl)-2,3,3-trimethyl indolium bromide (353 mg, 1.00 mmol), malonaldehyde bisphenylimine hydrochloride (259 mg, 1.00 mmol) and 1-sulphobutyl-2,3,3-trimethylindolium iodide (295 mg, 1.00 mmol) were dissolved in anhydrous pyridine (5 ml) and stirred at room temperature. Acetic anhydride (0.4 ml) was then added and the reaction stirred overnight at ambient temperature. The pyridine was removed in vacuo and the blue oil purified by flash column chromatography (dichloromethane-10% methanol gradient) to afford a blue solid (54 mg, 8%).

The Cy5 acid (49 mg, 0.08 mmol) was dissolved in anhydrous DMF under a nitrogen atmosphere then stirred at room temperature. DIPEA (12 µl, 0.09 mmol) and TSTU (27 mg, 0.09 mmol) were added and the reaction stirred for 2 hours until deemed complete to the NHS ester by tlc (20% MeOH/ 80% DCM). The NHS ester was treated with a second equivalent of DIPEA (12 µl, 0.09 mmol) and then aminoethylmaleimide (28 mg, 0.16 mmol) was added and the reaction allowed to stir for an additional 2 hours. Tlc showed conversion to a new product so the reaction was diluted with diethyl ether (50 ml) and the solvents decanted to leave a pink residue. Flash column chromatography (silica: DCM-40% methanol gradient) afforded the desired maleimide product (24 mg, 45%). UV/VIS (MeOH); absorption $\lambda_{max}$=644 nm. $\delta_H$ (300 MHz, CD$_3$OD) 8.21 (t, 2H), 7.54-7.26 (m, 8H), 6.80 (s, 2H), 6.64 (t, 1H), 6.38 (dd, 2H), 4.18 (m, 4H), 3.58 (m, 2H), 2.89 (m, 2H), 2.15 (t, 2H), 1.76 (s, 12H) and 2.06-1.39 (m, 10H).

xx) 1-(6-{[2-(2,5-Dioxo-2,5-dihydro-1H-pyrrol-1-yl)ethyl]amino}-6-oxohexyl)-2-[(1E,3E)-3-(1,3,3-trimethyl-5-sulpho-1,3-dihydro-2H-indol-2-ylidene)prop-1-enyl]-3,3-dimethyl-3H-indolium (Compound XI)

By similar methods, 1,2,3,3-tetramethyl-5-sulphonyl-indolium iodide and 1-(5-carboxypentyl)-2,3,3-trimethyl indolium bromide were reacted together with N,N'-diphenylformamidine to form the Cy3 acid, which when activated to the N-hydroxysuccinimide ester and treated with aminoethylmaleimide, was converted to 1-(6-{[2-(2,5-dioxo-2,5-dihydro-1H-pyrrol-1-yl)ethyl]amino}-6-oxohexyl)-2-[(1E,3E)-3-(1,3,3-trimethyl-5-sulpho-1,3-dihydro-2H-indol-2-ylidene)prop-1-enyl]-3,3-dimethyl-3H-indolium.

Example 2

2.1 Protein Isolation and Labelling

Initial experiments were performed on E. coli samples. E. coli strain ER1647 (Amersham Biosciences, Buckinghamshire, UK) was grown in glucose rich MOPS media at 37° C. overnight, followed by harvesting by centrifugation for 10 minutes at 4° C. at 12,000×g. The cell pellet was washed twice with wash buffer (10 mM Tris pH 8.0, 0.5 mM magnesium acetate). Cells were then resuspended in lysis buffer (8M urea, 4% w/v CHAPS, 40 mM Tris pH8.0) and lysed by sonication (3×10 second pulses on ice). The protein concentration of the E. coli lysate was determined using the Bio-Rad Dc Protein Assay as described by the manufacturer (Bio-Rad, Hertfordshire, UK).

Before use, the cyanine dyes were reconstituted in anhydrous DMF (Aldrich catalogue code 22,705-6) to give a final concentration of 10 mM (10 nmol/µl). The dye was vortexed briefly after addition of DMF to ensure the dye was completely dissolved. The reconstituted dye was stored at −20° C. and used within 2 weeks.

Disulphide bonds in 50 µg protein in lysis buffer were reduced by the addition of 10 nmol TCEP [tris-(2-carboxyethyl)phosphine] followed by incubation at 37° C. for 1 hour. Following reduction, 20 nmol reconstituted dye was added and incubated for 30 minutes at 37° C. The reaction was stopped with an equal volume of 2× sample buffer (Lysis buffer plus 20 mg/ml DTT and 4%(v/v) Pharmalytes 3-10). The samples were stored briefly on ice prior to first dimension separation or frozen protected from light for longer storage.

2.2 Preparation of Protein Samples for Separation

Equal amounts of protein samples labelled with Cy3 and Cy5 compounds I-XI were mixed to give the dye pair sets shown in Table 2.

TABLE 2

| Dye pair set | Compound |
| --- | --- |
| 1 | I |
|   | II |
| 2 | III |
|   | IV |
| 3 | I |
|   | V |
| 4 | VI |
|   | VII |
| 5 | VIII |
|   | IV |
| 6 | IX |
|   | X |
| 7 | VIII |
|   | II |
| 8 | IX |
|   | VII |
| 9 | III |
|   | II |
| 10 | VI |
|   | X |
| 11 | I |
|   | IV |
| 12 | XI |
|   | II |

2.3 Protein Separation by 2D Electrophoresis

2-D electrophoresis was performed using standard Amersham Biosciences 2D PAGE equipment and PlusOne™ reagents (Buckinghamshire, UK). Immobiline DryStrips (pH3-10 NL or pH 4-7 NL, 24 cm) were rehydrated overnight in 450 µl rehydration buffer (8M urea, 4% w/v CHAPS, 1% Pharmalytes (pH 3-10), 2 mg/ml DTT) overlaid with 2.5 ml DryStrip Cover Fluid, in an Immobiline DryStrip Reswelling Tray. Strips were focused using the Multiphor isoelectric focusing system. Prior to $2^{nd}$ dimension PAGE, each strip was equilibrated with 10 ml equilibration buffer A (8M urea, 100 mM Tris-HCl pH6.8, 30% v/v glycerol, 1% w/v SDS, 5 mg/ml DTT) on a rocking table for 10 minutes, followed by 10 ml equilibration buffer B (8M urea, 100 mM Tris-HCl pH6.8, 30% v/v glycerol, 1% w/v SDS, 45 mg/ml iodoacetamide) for a further 10 minutes. The strips were then loaded and run on 12% isochratic Laemmli SDS-PAGE gels.

2.4 Fluorescence Gel Imaging

Labelled proteins were visualised using the 2920 MasterImager (Amersham Biosciences, Buckinghamshire, UK) with the following settings:

|     | Excitation | Emission |
| --- | --- | --- |
| Cy3 | 540 nm (25 nmBP) | 590 nm (35 nmBP) |
| Cy5 | 620 nm (30 nmBP) | 680 nm (30 nmBP) |

Exposure times were optimised for individual experiments to give a maximum pixel value on the image of 50,000 to avoid saturation of the signal. Data from 2D-Master was exported as TIF files into Paintshop Pro™ to generate colour overlays for visual inspection. For detailed quantitative analysis of dye matching, gel images were exported into 2D Image Master software programme.

2.5 Image Analysis

Gel analysis in this study was performed using 2D Image Master (Amersham Biosciences, Buckinghamshire, UK) a 2-D analysis software platform. Following spot detection, the centre of each spot was used to generate pixel co-ordinates for each of the Cy3 and Cy5 images. The extent of migration matching was determined by comparing the co-ordinate positions of the centres of the Cy3 and Cy5 spots. This can be used to describe positional matching in terms of the number of matched spots within ±2 pixels of each other in both the x (pI) and y (mass) co-ordinates.

As both dyes have been used to label the same sample the same proteins are present in each labelled sample and thus if the dyes are matched for equivalent migration all of the spots should exactly overlay between the 2 images. The % of spots within +/−2 pixels was measured to determine the overall matching.

Example 3

Difference Gel Electrophoresis of Dyes Matched for Saturation Labelling on Cysteine Residues by Variation of the Alkyl Chain Length (r)

Dye structure effects were tested by labelling the same complex protein sample (E. coli lysate) with each dye, mixing the Cy3 and Cy5 labelled samples and separating by 2D electrophoresis. Following fluorescence scanning, the images were overlayed and analysed as described in the above example.

E. coli lysate was labelled with Cy3 compounds and Cy5 compounds as described. The labelled samples were mixed prior to separation to give dye sets 1, 2, 9, 11 and 12 to show the effect of varying the length of the alkyl chain by the addition of $CH_2$ units. Table 3 shows the quantitative positional data following analysis of the overlaid images of protein labelled with dye sets 1, 2, 9, 11 and 12.

TABLE 3

Effect of Varying Alkyl Chain Length (r) on Positional Matching

| Dye Set | Value of n | p | q | r | Matched Spots within 2 Pixels (%) | |
|---|---|---|---|---|---|---|
| | | | | | X (pI) | Y (mass) |
| 1 | 1 (Cy3) | 5 | 2 | 2 | 82.7 | 88.8 |
| | 2 (Cy5) | 5 | 2 | 1 | | |
| 2 | 1 (Cy3) | 5 | 2 | 3 | 79.7 | 77.7 |
| | 2 (Cy5) | 5 | 2 | 2 | | |
| 9 | 1 (Cy3) | 5 | 2 | 3 | 76 | 76.3 |
| | 2 (Cy5) | 5 | 2 | 1 | | |
| 11 | 1 (Cy3) | 5 | 2 | 2 | 86.1 | 44.3 |
| | 2 (Cy5) | 5 | 2 | 2 | | |
| 12 | 1 (Cy3) | 5 | 2 | 1 | 59.7 | 58.9 |
| | 2 (Cy5) | 5 | 2 | 1 | | |

Thus, when the Cy3 and Cy5 have equal alkyl chains (e.g. dye sets 11 and 12) the overall mass of Cy3 is decreased relative to Cy5. This results in poor positional matching in the mass dimension. When there is a two carbon unit difference in the alkyl chain length (e.g. dye set 9), mass matching improves. Optimum matching for both mass and pI is obtained when there is a single carbon atom difference between the dyes e.g. dye set 1 and 2). The preferred dye set is dye set 1. This shows that migration matching using a single carbon unit difference in the linker r gives good positional matching of differentially labelled proteins on 2D electrophoresis.

FIG. 2 shows overlay images of proteins labelled with dye sets 1, 12 and 9 and separated by 2D electrophoresis with outlines of labelled protein spots to demonstrate the positional matching. The overlays are taken from a portion of a 2D electrophoresis gel of E. coli lysate labelled with Cy3 or Cy5 showing the ~20-30 kDa mass range and ~5.5-6.0 pI range. The circles representing the outline positions of the protein spots for both the Cy3 and Cy5 labelled proteins (arrowed) were determined using the 2D ImageMaster software. Dye set 12 gives poor mass matching as the Cy5 labelled proteins run below the Cy3 labelled proteins (example arrowed). Dye set 9 also shows poor mass matching, in this case with the Cy5 labelled proteins running above the Cy3 labelled proteins (example arrowed). Preferred dye set 1 gives the optimal positional matching.

Example 4

Difference Gel Electrophoresis of Dyes Matched for Saturation Labelling on Cysteine Residues by Variation of the Length of the Linker to the Indole Nucleus (p)

E. coli lysate was labelled with Cy3 and Cy5 compounds and samples mixed to give dye sets 1 and 3 as described. Table 4 shows the quantitative positional data following analysis of the overlaid images of protein labelled with these dye sets.

TABLE 4

Effect of Varying Linker Length (p) on Positional Matching

| Dye Set | Value of n | p | q | r | Matched Spots within 2 Pixels (%) | |
|---|---|---|---|---|---|---|
| | | | | | X (pI) | Y (mass) |
| 1 | 1 (Cy3) | 5 | 2 | 2 | 87.3 | 86.4 |
| | 2 (Cy5) | 5 | 2 | 1 | | |
| 3 | 1 (Cy3) | 5 | 2 | 2 | 88.1 | 85.2 |
| | 2 (Cy5) | 4 | 2 | 2 | | |

This shows that migration matching using a single carbon unit difference in the linker p gives good positional matching of differentially labelled proteins on 2D electrophoresis.

Example 5

Difference Gel Electrophoresis of Dyes Matched for Saturation Labelling on Cysteine Residues by Variation of the Length of the Linker to the Maleimide Group (q)

Variation of the linker q was achieved by increasing the length of the linker by a single $CH_2$ unit from an aminoethyl to aminopropyl maleimide. E. coli lysate was labelled with Cy3 and Cy5 compounds and samples mixed to give dye sets 1, 5 and 7 as described. Table 5 shows the quantitative positional data following analysis of the overlaid images of protein labelled with these dye sets.

TABLE 5

Effect of Varying Maleimide Linker Length (g) on Positional Matching

| Dye Set | Value of n | p | q | r | Matched Spots within 2 Pixels (%) | |
|---|---|---|---|---|---|---|
| | | | | | X (pI) | Y (mass) |
| 1 | 1 (Cy3) | 5 | 2 | 2 | 85.7 | 88.0 |
| | 2 (Cy5) | 5 | 2 | 1 | | |
| 5 | 1 (Cy3) | 5 | 3 | 2 | 64.2 | 80.7 |
| | 2 (Cy5) | 5 | 2 | 2 | | |
| 7 | 1 (Cy3) | 5 | 3 | 2 | 67.6 | 71.8 |
| | 2 (Cy5) | 5 | 2 | 1 | | |

Thus, the aminoethyl linker (dye set 1) has improved pI matching compared to the aminopropyl linker (dyes sets 5 and 7) possibly due to the β-effect. When there is a two carbon unit difference between the dyes the mass matching also decreases (dye set 7). When there is a single carbon unit difference mass matching improves. Thus, an aminoethyl maleimide linker (q=2) is preferred for pi matching.

Example 6

Difference Gel Electrophoresis of Dyes Matched for Saturation Labelling on Cysteine Residues by Variation of the Position of the Sulphonate Group Sulphonated cyanine dyes generally have the sulphonate group directly attached to the indole ring as in dye set 1. Variation of the sulphonate position was achieved by attaching the sulphonate to the ring via a butyl chain linker. E. coli lysate was labelled with Cy3 and Cy5 compounds and samples mixed to give dye sets 1, 4, 6, 8 and 10 as described.

Table 6 shows the quantitative positional data following analysis of the overlaid images of protein labelled with these dye sets.

TABLE 6

Effect of Varying Sulphonate Position on Matching

| Dye Set | Sulphonate Position | Value of n | p | q | r | Matched Spots within Pixels (%) | |
|---|---|---|---|---|---|---|---|
| | | | | | | X (pI) | Y (mass) |
| 6 | Pendant | 1 (Cy3) | 5 | 3 | 4 | 86.3 | 82.6 |
| | Pendant | 2 (Cy5) | 5 | 2 | 4 | | |
| 4 | Pendant | 1 (Cy3) | 5 | 2 | 4 | 78.3 | 79.7 |
| | Pendant | 2 (Cy5) | 4 | 2 | 4 | | |
| 8 | Pendant | 1 (Cy3) | 5 | 3 | 4 | 73.3 | 63.7 |
| | Pendant | 2 (Cy5) | 4 | 2 | 4 | | |
| 10 | Pendant | 1 (Cy3) | 5 | 2 | 4 | 82.4 | 49.8 |
| | Pendant | 2 (Cy5) | 5 | 2 | 4 | | |

Comparison with previous data shows that the removal of the sulphonate from the ring system to a pendant butyl chain does appear to change the pI matching. The matching in the mass dimension is no better than that achieved with dye set 1. Where there is no compensation for the difference n between the dyes the migration matching decreases (dye set 10). When there is a two carbon unit difference (dye set 8), mass matching is decreased compared to dye set 1. When there is a single carbon unit difference (dye sets 4 and 6) matching is improved. The best combination with a pendant butyl sulphonate is to modify the linker q to the maleimide (dye set 6).

What is claimed is:

1. A matched set of fluorescent dyes comprising two or more different fluorescent dyes of formula (I):

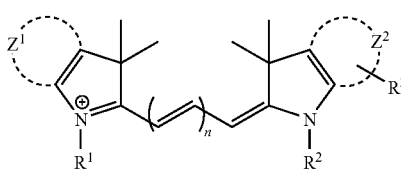

wherein n is different for each said dye and is 1, 2, or 3;
$Z^1$ and $Z^2$ independently represent the carbon atoms necessary to complete a phenyl or naphthyl ring system;
one of groups $R^1$ and $R^2$ is the group:

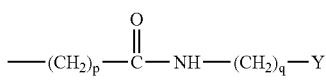

where Y is a target bonding group and in each dye of the set of dyes is the same and is selected from the group consisting of maleimido groups and iodoacetamido groups;
remaining group $R^1$ or $R^2$ is selected from —$(CH_2)_4$—W or —$(CH_2)_r$—H;
group $R^3$ is hydrogen, except when either $R^1$ or $R^2$ is —$(CH_2)_r$—H, in which case $R^3$ is W;
W is selected from sulphonic acid and sulphonate;
p is an integer from 3 to 6;
q is 2 or 3; and
r is an integer from 1 to 5;
and salts thereof and further wherein when n of two of said dyes differs by +1, one of p, q and r of said two dyes differs by −1.

2. A matched set of fluorescent dyes comprising at least two different fluorescent dyes of formula (II):

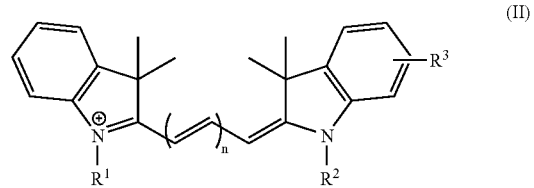

wherein n is different for each said dye and is 1, 2, or 3;
one of groups $R^1$ and $R^2$ is the group:

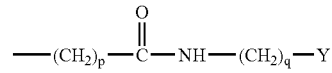

where Y is a target bonding group and in each dye of the set of dyes is the same and is selected from the group consisting of maleimido groups and iodoacetamido groups;
remaining group $R^1$ or $R^2$ is selected from —$(CH_2)_4$—W or —$(CH_2)_r$—H;
group $R^3$ is hydrogen, except when either $R^1$ or $R^2$ is —$(CH_2)_r$—H, in which case $R^3$ is W;
W is selected from sulphonic acid and sulphonate;
p is an integer from 3 to 6;
q is 2 or 3; and
r is an integer from 1 to 5;
and salts thereof;
and further wherein when n of two of said dyes differs by +1, one of p, q and r of said two dyes differs by −1.

3. The matched set of dyes of claim 1 or claim 2 comprising at least two different fluorescent dyes wherein:
n is 1 or 2;
p is 4 or 5;
q is 2 or 3; and
r is 1, 2 or 3.

4. The matched set of dyes of claim 1 or claim 2, wherein in each said dye Y is a maleimido group.

5. The matched set of dyes of claim 1 or claim 2 wherein said salts are selected from salts K$^+$, Na$^+$, NH$_4^+$, or containing (R)$_3$NH$^+$ and (R)$_4$N$^+$ wherein R is C$_1$ to C$_4$ alkyl.

6. A matched set of dyes selected from the group consisting of:
Set 1
1-(6-{[2-(2,5-dioxo-2,5-dihydro-1H-pyrrol-1-yl)ethyl]amino}-6-oxohexyl)-2-[(1E,3E)-3-(1-ethyl-3,3-dimethyl-5-sulpho-1,3-dihydro-2H-indol-2-ylidene)prop-1-enyl]-3,3-dimethyl-3H-indolium (Compound I); and
1-(6-{[2-(2,5-dioxo-2,5-dihydro-1H-pyrrol-1-yl)ethyl]amino}-6-oxohexyl)-3,3-dimethyl-2-[(1E,3E,5E)-5-(1,3,3-trimethyl-5-sulpho-1,3-dihydro-2H-indol-2-ylidene)penta-1,3-dienyl]-3H-indolium (Compound II);
Set 2
1-(6-{[2-(2,5-dioxo-2,5-dihydro-1H-pyrrol-1-yl)ethyl]amino}-6-oxohexyl)-2-[(1E,3E)-3-(1-propyl-3,3-dimethyl-5-sulpho-1,3-dihydro-2H-indol-2-ylidene)prop-1-enyl]-3,3-dimethyl-3H-indolium (Compound III); and 1-(6-{[2-(2,5-dioxo-2,5-dihydro-1H-pyrrol-1-yl)ethyl]
amino}-6-oxohexyl)-3,3-dimethyl-2-[(1E,3E,5E)-5-(1-
ethyl-3,3-trimethyl-5-sulpho-1,3-dihydro-2H-indol-2-
ylidene)penta-1,3-dienyl]-3H-indolium (Compound
IV);

Set 3

1-(6-{[2-(2,5-dioxo-2,5-dihydro-1H-pyrrol-1-yl)ethyl]
amino}-6-oxohexyl)-2-[(1E,3E)-3-(1-ethyl-3,3-dim-
ethyl-5-sulpho-1,3-dihydro-2H-indol-2-ylidene)prop-
1-enyl]-3,3-dimethyl-3H-indolium (Compound I); and 1-(5-{[2-(2,5-dioxo-2,5-dihydro-1H-pyrrol-1-yl)ethyl]
amino}-6-oxopentyl)-3,3-dimethyl-2-[(1E,3E,5E)-5-
(1-ethyl-3,3-trimethyl-5-sulpho-1,3-dihydro-2H-indol-
2-ylidene)penta-1,3-dienyl]-3H-indolium (Compound
V);

Set 4

1-(6-{[2-(2,5-dioxo-2,5-dihydro-1H-pyrrol-1-yl)ethyl]
amino}-6-oxohexyl)-2-[(1E,3E)-3-(3,3-dimethyl(1-
sulpho-butyl)-1,3-dihydro-2H-indol-2-ylidene)prop-1-
enyl]-3,3-dimethyl-3H-indolium (Compound VI); and 1-(5-{[2-(2,5-dioxo-2,5-dihydro-1H-pyrrol-1-yl)ethyl]
amino}-6-oxopentyl)-3,3-dimethyl-2-[(1E,3E,5E)-5-
(3,3-dimethyl-(1-sulpho-butyl)-1,3-dihydro-2H-indol-
2-ylidene)penta-1,3-dienyl]-3H-indolium (Compound
VII);

Set 5

1-(6-{[3-(2,5-dioxo-2,5-dihydro-1H-pyrrol-1-yl)propyl]
amino}-6-oxohexyl)-2-[(1E,3E)-3-(1-ethyl-3,3-dim-
ethyl-5-sulpho-1,3-dihydro-2H-indol-2-ylidene)prop-
1-enyl]-3,3-dimethyl-3H-indolium (Compound VIII);
and 1-(6-{[2-(2,5-dioxo-2,5-dihydro-1H-pyrrol-1-yl)ethyl]
amino}-6-oxohexyl)-3,3-dimethyl-2-[( 1E,3E,5E)-5-
(1-ethyl-3,3-trimethyl-5-sulpho-1,3-dihydro-2H-indol-
2-ylidene)penta-1,3-dienyl]-3H-indolium (Compound
IV); and Set 6

1-(6-{[3-(2,5-dioxo-2,5-dihydro-1H-pyrrol-1-yl)propyl]
amino}-6-oxohexyl)-2-[(1E,3E)-3-(3,3-dimethyl(1-
sulpho-butyl)-1,3-dihydro-2H-indol-2-ylidene)prop-1-
enyl]-3,3-dimethyl-3H-indolium (Compound IX); and 1-(6-{[2-(2,5-dioxo-2,5-dihydro-1H-pyrrol-1-yl)ethyl]
amino}-6-oxohexyl)-3,3-dimethyl-2-[(1E,3E,5E)-5-(3,
3-dimethyl-(1-sulpho-butyl)-1,3-dihydro-2H-indol-2-
ylidene)penta-1,3-dienyl]-3H-indolium (Compound
X).

7. A kit comprising a matched set of fluorescent dyes
comprising at least two different fluorescent dyes having the
formula (I):

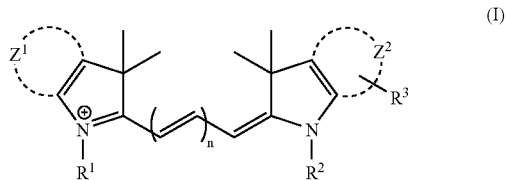

wherein n is different for each said dye and is 1, 2, or 3;
$Z^1$ and $Z^2$ independently represent the carbon atoms nec-
essary to complete a phenyl or naphthyl ring system;
one of groups $R^1$ and $R^2$ is the group:

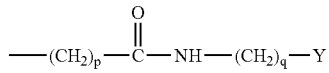

where Y is a target bonding group and in each dye of the set
of dyes is the same and is selected from the group con-
sisting of maleimido groups and iodoacetamido groups;
remaining group $R^1$ or $R^2$ is selected from —$(CH_2)4$—W
or —$(CH_2)_r$—H;
group $R^3$ is hydrogen, except when either $R^1$ or $R^2$ is
—$(CH_2)_r$—H, in which case $R^3$ is W;
W is selected from sulphonic acid and sulphonate;
p is an integer from 3 to 6;
q is 2 or 3; and
r is an integer from 1 to 5;
and salts thereof;
and further wherein when n of two of said dyes differs by
+1, one of p, q and r of said two dyes differs by −1.

* * * * *